United States Patent [19]

Chambers

[11] Patent Number: 4,841,244

[45] Date of Patent: * Jun. 20, 1989

[54] METHOD AND APPARATUS FOR ON-LINE MONITORING OF WEAR IN MACHINERY

[75] Inventor: Keith W. Chambers, Pinawa, Canada

[73] Assignee: Her Majesty the Queen in Right of Canada as Represented by the Minister of National Defence, Canada

[*] Notice: The portion of the term of this patent subsequent to Mar. 17, 2004 has been disclaimed.

[21] Appl. No.: 908,731

[22] Filed: Sep. 18, 1986

[30] Foreign Application Priority Data

Oct. 11, 1985 [CA] Canada ................................. 492,775

[51] Int. Cl.$^4$ ..................... G01N 27/74; G01R 33/12; G01F 1/708; G01P 5/18
[52] U.S. Cl. .................................... 324/204; 324/227; 73/861.05
[58] Field of Search ............... 324/204, 227, 236, 262, 324/445, 71.1, 71.4; 73/861.05, 861.11; 340/631, 64

[56] References Cited

U.S. PATENT DOCUMENTS

| | | | |
|---|---|---|---|
| 2,671,200 | 3/1954 | Lederer | 324/234 X |
| 3,233,173 | 2/1966 | Lees et al. | 324/234 X |
| 3,347,087 | 10/1967 | Engelhardt et al. | 324/201 X |
| 3,748,576 | 7/1973 | Sigournay | 340/631 X |
| 4,100,491 | 7/1978 | Newman, Jr. et al. | 324/204 |
| 4,219,805 | 8/1980 | Magee et al. | 340/631 |
| 4,536,713 | 8/1985 | Davis et al. | 324/204 X |
| 4,541,530 | 9/1985 | Kenny et al. | 324/233 X |
| 4,651,091 | 3/1987 | Chambers et al. | 324/227 X |
| 4,651,092 | 3/1987 | Brunsch et al. | 324/239 X |
| 4,686,469 | 8/1987 | Lewis | 324/204 |
| 4,692,698 | 9/1987 | Lewis | 324/235 X |

OTHER PUBLICATIONS

M. C. Arneson, K. W. Chambers, I. M. Smith and J. E. Swiddle, "Probe for Determining the Concentration of Ferromagnetic Particles in Water at High Temperature and Pressure", *Power Industry Research,* (1981):87–90.

Primary Examiner—Gerard R. Strecker
Assistant Examiner—Warren S. Edmonds
Attorney, Agent, or Firm—Gerald J. Ferguson, Jr.

[57] ABSTRACT

A detector for producing an electrical signal proportional to the concentration of ferromagnetic particulate material in a fluid stream includes a sensing coil arranged to form the inductance coil of a radio frequency oscillator arranged to produce an electrical signal at a base frequency, a magnetic trap for producing a magnetic field and a support for supporting the sensing coil and the magnetic trap in juxtaposition to one another such that, when the coil is disposed within or proximate the fluid stream and electrically connected to the oscillator, energization of the magnetic trap causes ferromagnetic particulate material proximate the coil to be attracted toward the coil resulting in a deviation of the frequency of the signal from the base frequency proportional to the concentration of ferromagnetic particulate material in the fluid stream. The detector has particular utility in monitoring wear in machines employing a lubricating fluid for lubricating ferromagnetic components which produce ferromagnetic particulate wear debris during operation.

32 Claims, 2 Drawing Sheets

METHOD AND APPARATUS FOR ON-LINE MONITORING OF WEAR IN MACHINERY

This invention relates, in general, to an improved method and apparatus for determining a quantity proportional to the concentration of ferromagnetic particulate material in a fluid and, more specifically, to an improved method and apparatus for monitoring the health and/or the degree of wear of a machine having ferromagnetic components subjected to wear during operation and a fluid lubrication system for lubricating the ferromagnetic components.

BACKGROUND OF THE INVENTION

Canadian Patent Application Serial No. 439,146, filed on Oct. 17, 1983 by the present applicant, describes a novel method and apparatus for monitoring the health and/or degree of wear of machinery. The primary objective of such apparatus is to maximze human safety by forestalling failure and minimize downtime and its associated expense and inconvenience.

In essence, the described method is based on the premises that (a) wear debris concentration and particle size increase as the rate of wear increases, (b) the frequency of the output signal of an oscillator is directly related to the permeability of the inductance coil of the oscillator, and (c) the permeability is related to the mass of ferromagnetic material in the core of the coil. The method involves passing a stream of a fluid containing ferromagnetic particulate material, the concentration of which is to be determined, through a flow tube having an electromagnetic trap disposed about the flow tube upstream of a sensing ciol also disposed about the flow tube. The sensing coil forms part of an oscillator circuit which, in turn, forms part of a larger electrical circuit which monitors and processes the output of the oscillator. At predetermined time intervals, the electromagnet is energized for a period of time to trap ferromagnetic particulate material on the inside of the flow tube. De-energization of the electromagnet releases the trapped material into the fluid stream toward the sensing coil. Flow of the accumulation passed the sensing coil causes a slight reduction in the frequency of the signal of the oscillator and the magnitude of the change of the frequency together with the elapsed time within which the fluid passes through the sensing coil are employed to determine the concentration of the ferromagnetic particulate material in the fluid. Thus, the change in frequency is determined as a transient signal following the trapping event.

While the method and apparatus operate quite successfully, the process for determining the concentration is somewhat complex and the detector is relatively bulky.

SUMMARY OF THE INVENTION

The present invention seeks to simplify the method of, generally, detecting the concentration of ferromagnetic particulate material in a fluid and, specifically, monitoring the health of machinery by monitoring a parameter or quantity which is linearly related to the concentration of ferromagnetic particulate material in the lubricant circulating system. The present invention also seeks to provide a detector which is more compact and sensitive than known detectors of the type with which the present invention is concerned. This is made possible by trapping the ferromagnetic particulate material against or proximate the sensing coil winding and by detecting the deviation of the oscillator output signal from a reference point while the trapping process is in progress.

It has been determined that there is a marked trend towards improved detector sensitivity with decreasing values of the distance between the magnetic trap and the sensing coil. This can be explained in terms of the changes in the shape of the plume of the material released by the trap. When the trap is de-energized, the released material initially moves downstream as a thin, cohesive film against the side wall of the flow tube but, as it moves downstream, the plume progressively disperses throughout the bore of the flow tube. Experimental evidence suggests that the sensitivity of the detector is very much greater when the released material is distributed as a uniform film against the inside wall of the tube, as close to the coil windings as possible, than when the material is distributed across the bore of the flow tube. Thus, the interaction of the radio frequency field with material in the bore of the coil is more drastically changed for a given mass of material within the bore when all of the material is located on the inside wall of the coil as compared with the same mass uniformly dispersed throughout the core volume. It will be seen, therefore, that the detector arrangement disclosed in the aforementioned application is not an optimum arrangement where high sensitivity is desired.

Thus, by reducing the separation between the trap and the coil to zero, i.e. by locating the coil between the poles of the magnetic trap, it has been found that the sensitivity of the detector can be increased by a factor of about 1000. This change not only allows the method of determining the concentration of ferromagnetic particulate material in the fluid to be simplified in that the determination of the change in frequency is effected concurrently with trapping as explained more fully later, it also allows the detector to be made much more compact because the trap and sensing coil can be integrated into a single unit.

In accordance with one aspect of the present invention there is provided a device for producing an electrical signal which is proportional to the concentration of ferromagnetic particulate material in a fluid stream, the device comprising, in combination, a sensing coil arranged to form the inductance coil of and adapted to be connected to a radio frequency oscillator arranged to produce an electrical signal at a base frequency, magnetic trap means for producing a magnetic field and support means for supporting the sensing coil and the magnetic trap means in juxtaposition to one another such that, when the coil is disposed within or proximater the fluid stream and electrically connected to the oscillator, energization of the magnetic trap means causes ferromagnetic particulate material proximate the coil to be attracted toward the coil resulting in a deviation of the frequency of the signal from the base frequency proportional to the concentration of ferromagnetic particulate material in the fluid stream.

In accordance with another aspect of the invention, there is provided a method of determining a quantity related to the concentration of ferromagnetic material in a fluid, comprising the steps of (a) passing a sample of the fluid through a fluid conduit, (b) magnetically trapping ferromagnetic particulate material at a predetermined site in the fluid conduit at which an inductance coil of a radio frequency oscillator is coaxially disposed, (c) determining the deviation, during the trapping step, of the output signal of the oscillator from a reference signal, and (d) determining the ratio of the deviation to the duration of the deviation, the ratio being linearly proportional to the concentration of the ferromagnetic particulate material in the fluid.

BRIEF DESCRIPTION OF THE DRAWINGS

These and other features of the invention will become more apparent from the following description in which reference is made to the appended drawings, wherein.

DETAILED DESCRIPTION OF A PREFERRED EMBODIMENT

Figure 1:
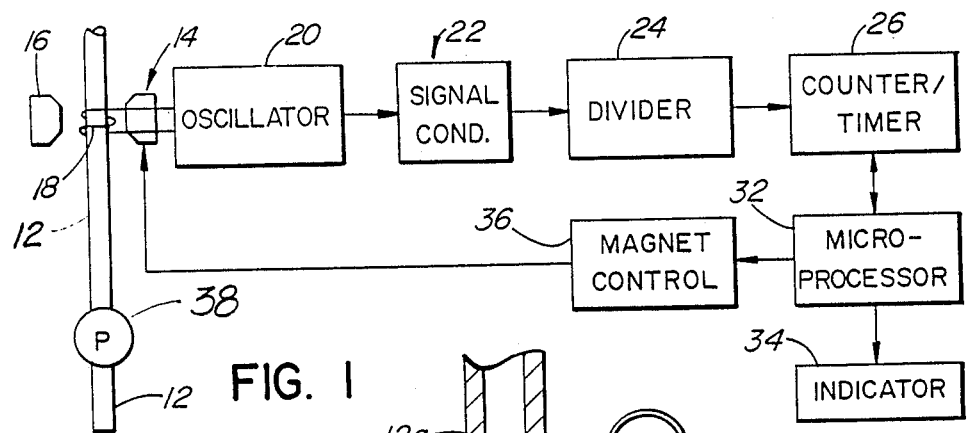
FIG. 1 is a block diagram of a mechanical and electrical circuit in which the detector of the present invention is located.

With reference to FIG. 1 of the drawings, there is provided a flow tube 12 through which a fluid containing ferromagnetic particulate material, the relative concentration of which is to be determined, is passed. A detector, generally indicated by reference numeral 14, includes a magnet means 16 and a sensing coil 18 arranged to be coaxially disposed at a common site with respect to the flow tube. The sensing coil forms part of a sensing oscillator 20 whose output is fed to a signal conditioning circuit, generally designated by reference numeral 22, and a divider 24. The output of divider 24 is fed to a counter/timer 26 which is controlled by a microprocessor 32. The microprocessor is arranged to compute a parameter or quantity related to the concentration of the ferromagnetic particulate material in the fluid on the basic of the response of the oscillator to the accumulation of trapped ferromagnetic particulate material during a material trapping interval. The microprocessor may quantitatively or qualitatively display the parameter in appropriate form on an indicator 34.

A magnet control circuit 36 is provided for selectively energizing and de-energizing the trapping magnet. For the purpose of monitoring the rate of wear of a machine, the microprocessor is arranged to signal, at predetermined timed intervals, control circuit 36 to energize and de-energize the magnet. A pump 38 may be provided for pumping the fluid through the flow tube.

In order to determine the concentration of ferromagnetic particulate material in a fluid in accordance with the method of the present invention, fluid is caused to flow through the flow tube and the magnet is energized by the microprocessor via magnet control 36. The timer activated one or two seconds later. When the magnet trapping field is established, ferromagnetic particulate material in the fluid accumulates on the inside of the flow tube adjacent the sensing coil.

Figure 4:
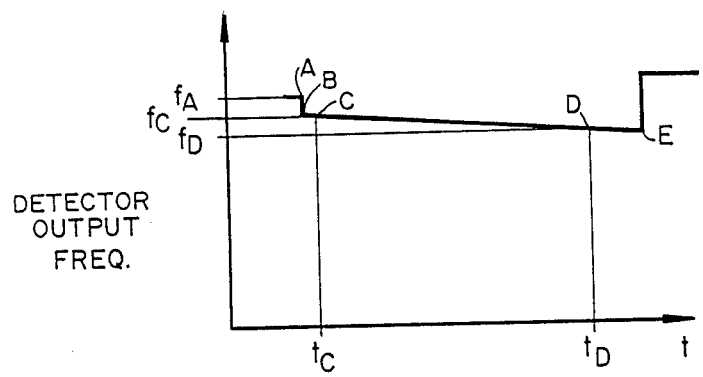
FIG. 4 is a frequency vs. time profile of the output of an oscillator, whose inductance coil is coaxially disposed with respect to a flow tube at a trapping site, during a trapping cycle.

FIG. 4 illustrates in graphical form the frequency response of the oscillator as a function of the time of trapping and release of ferromagnetic particulates. Prior to establishing the magnetic field, the stready state frequency of the output signal of the oscillator is $f_A$, about 34 MHz, but the oscillator output experiences a step change from $f_A$ to $f_B$ as soon as the magnet is energized. The frequency thereafter gradually changes from $f_B$ to $f_E$ as particles of ferromagnetic material are progressively trapped against the inside of the flow tube. The rate at which this takes places is a function of the concentration of ferromagnetic particulate material. Finally, the oscillator frequency returns to $f_A$ when the trapping magnet is de-energized. The trapped ferromagnetic particulate material is released into the fluid stream.

The timer is activated at $t_C$, about one or two seconds after the trapping magnet field had been established to allow the oscillator electronics to settle, and de-activated at $t_D$. The trapping magnet field is reduced to zero one or two seconds later. The trapping interval may vary from as little as one or two seconds for very high concentrations to 120 seconds or more for very low concentrations of ferromagnetic particulates in the fluid.

At least during the trapping interval $t_c$–$t_D$, the output of the sensing oscillator is continuously fed to the signal conditioner and divider. The signal conditioner filters the oscillator output to remove unwanted noise and the like and amplifies the signal so as to place it within the input specification range of the divider. The divider reduces the oscillator frequency from a base frequency or about 34 MHz to about to a frequency of about 1.1 MHz so as to provide a signal which is compatible with the counter/timer input specifications and feeds the signal, via the counters, to the microprocessor.

It can be shown that the radio of the change or deviation, $f_c$–$f_D$, of the frequency to the trapping interval is, within limits, linearly related to the concentration of the ferromagnetic particulate material in the fluid stream and the actual or numerical value of the concentration can be determined simply by multiplying the ratio by an appropriate constant. Thus, it will be seen that the determination of the concentration of ferromagnetic particulate material in a fluid in accordance with the present invention is a relatively simple process.

There are generally four ways in which the output of the oscillator and the trapping interval may be advantageously used to compute the concentration of the ferromagnetic particulate material. A first method involves determining the frequencies $f_C$ and $F_D$ for a predetermined, fixed trapping interval, $t_C$–$t_D$. A second method involves determining the elapsed trapping interval for the frequency to attain a preselected frequency $f_D$. A thrid method, related to the first, involves counting the number of cycles of the frequency which occur during a preselected trapping interval. The fourth, related to the second method, involves determining the trapping interval for the cycle count to attain a predetermined value N.

As suggested above, there are natural limits within which the frequency ramp is linear with respect to the trapping interval. Employing the first and third methods discussed above without taking appropriate precautions may result in the device operating in a non-linear range and this will produced inaccurate results. In order to ensure that the dector always operates within the linear trapping range, regardless whether the ferromagnetic particulate material concentration is low or high, the preferred mode of operation of the detector is the fourth method, i.e. determining the trapping interval for a predetermined valve of cycle count, N.

For the particular detector described later, a cycle count of 200,000 has been deemed to be a suitable count since it represents a reasonable compromise between a desire for high precision (high counts but long trapping interval) and short analysis time (low counts but short trapping time). The important criterion, as suggested above, is that the detector operate within its linear range, i.e., the range within which the detector response increases linearly with the trapping interval and/or conncentration of suspended ferromagnetic material in the field in the flow tube. This determines the upper limit that the fixed cycle count can take. While that limit has not been determined for the specific apparatus referenced later, it is though to be at least as high as 2,700,000.

Once the microprocessor computes the ratio on the basis of the predetermined cycle count, N, and the determined trapping interval, the concentration is determined, as before, simply by multiplying the ratio by a constant. This method simplifies the process even further since all that is required to determine the concentration is to multiply the determined trapping interval by a constant comprised of a calibration constant and the fixed, predetermined value of the cycle count. Since the trapping interval can be determined very accurately, the determined value of concentration or a quantity linearly related to concentration is precise.

Figure 5:
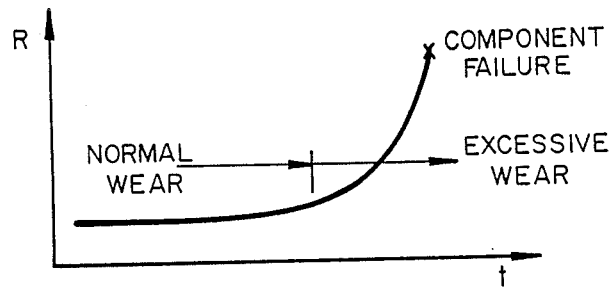
FIG. 5 is a graph which diagrammatically illustrates a typical response, R, of the detector as a machine to which the detector is connected approaches failure.

In order to monitor the health of a machine 40, the flow tube is connected into the lubrication system of the machine, as shown in phantom lines in FIG. 1, and then all that is required is to monitor the rate of change of the concentration or a quantity linearly related to concentration of the ferromagnetic particulate material in the lubricating fluid of the machine. FIG. 5 graphically illustrates a typical response, R, of the detector connected to a machine. Initially, the rate of change of the concentration or ratio is very small and linear. This is indicative of normal wear. However, as the machine or a ferromagnetic component in the machine begins to fail, the response becomes non-linear and increases at a relatively rapid rate.

Thus, the conncentration, or above mentioned ratio, is determined at predetermined equal time intervals, such as, for example, every 25 seconds. On each occasion, the microprocessor computes and stores the concentration or ratio. When at least three values of concentration or ratio have been determined, the microprocessor determines the rate of change of the concentration or ratio. The microprocessor may be programmed to activate an alarm, such as a light or buzzer, to alert the machine operator in the event that the rate of change of concentration exceeds a predetermined value, which value will depend on factors related to the nature of the machine.

Figure 2:
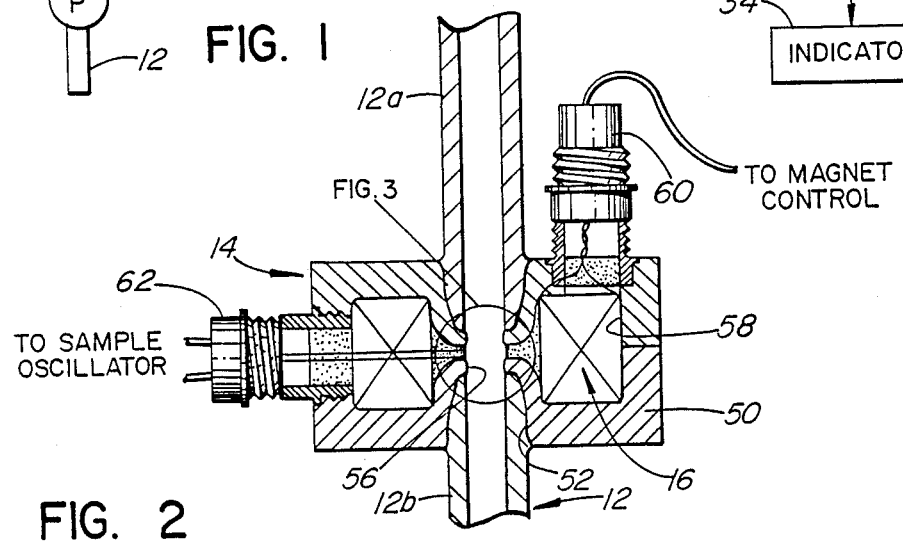
FIG. 2 is a longitudinal cross-sectional view of a detector constructed in accordance with the present invention.
Figure 3:
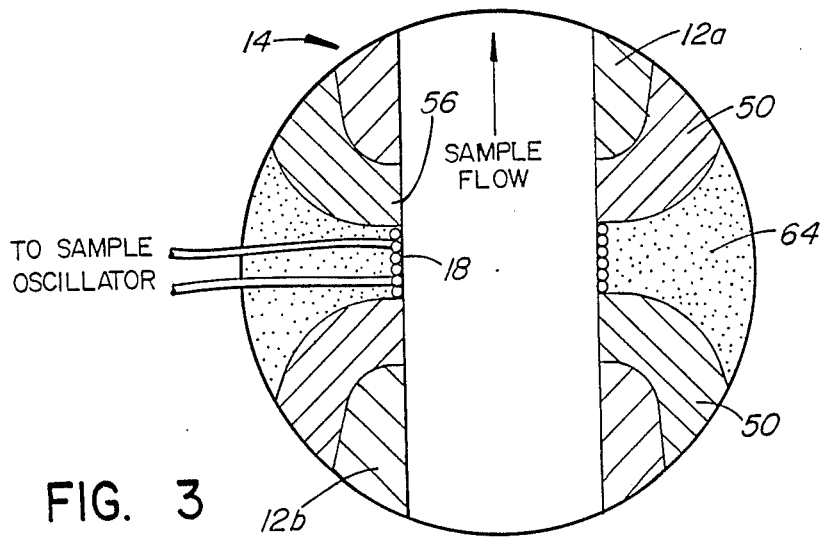
FIG. 3 is an enlarged, broken, cross-sectional view illustrating the inductance coil defining part of a fluid flow passage.

With reference to FIGS. 2 and 3, the detector 14 will be seen to be comprised of a radially split, generally cylindrical housing or magnet yoke 50, formed of soft iron (magnet iron). The housing has an outside diameter of about one inch. It is formed with a fluid inlet 52, a fluid outlet 54 and a fluid passage 56 connecting the fluid inlet and the fluid outlet. The diameter of the passage is about one-eighth of one inch. The inlet and outlet are silver soldered or otherwise secured to the ends of flow tube portions 12a and 12b. The other ends of the flow tubes are arranged to be connected to a source of fluid containing the ferromagnetic particulate material.

The magnet yoke is formed with a generally annular chamber 58 which is concentric with respect to the fluid passage and receives electromagnet 16 in the form of 600 turns of #33 AWG enamelled copper wire. A connector 60 is secured to the magnet yoke and serves to connect the magnet winding to magnet control 36, located at a remote site, so that the magnet can be selectively energized and de-energized. Sensing coil 18, in the form of 10 turns of #40 AWG enamelled copper wire, is concentrically disposed within the electromagnet between the poles thereof by means of a non-magnetic, electrically insulating material 64, such as an epoxy matrix. As best shown in FIG. 3, the coil itself forms part of the fluid passage. Since there is no intervening material, such a glass or other conduit, between the coil and the fluid, trapped ferromagnetic particulate material accumulated against the coil itself and this results in a significant increase in the sensitivity of the detector. A connector 62 serves to connect the leads of coil 18 to the oscillator which is secured to the magnet yoke so that the trapping magnet, the sensing coil and the oscillator form an integral assembly. Leads, not shown, extend from the oscillator to the signal conditioner located at a remote site.

As will be appreciated by those skilled in this art, the sensitivity of the detector will be proportional to the base frequency of the oscillator and, accordingly, the base frequency should be as high as possible subject to the availability of downstream components capable of handling very high frequencies.

The details of the hardward and software associated with the micorprocessor do not in themselves form part of the present invention and, therefore, have not been described in detail. However, reference may be had to the aforementioned application in which more detail has been present in this regard.

Figure 6:
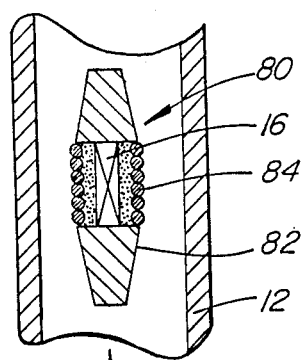
FIGS. 6 and 7 are diagrammatically illustrate alternative embodiments of the detector.
Figure 7:
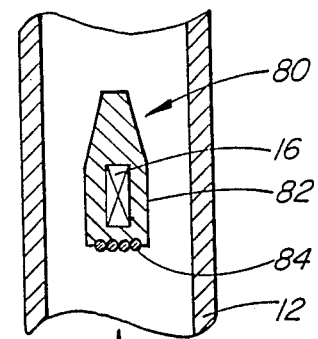

FIGS. 6 and 7 diagrammatically illustrate alternative embodiments of the detector. In both cases, the detector is in the form of a probe which may be suitably secured within a fluid conduit. In FIG. 6, the detector 80 is comprised of a housing 82 in which a trapping magnet is disposed while a sensing coil 84 is coaxially disposed about the magnet in electrically insulates relation and wound about the surface of the housing. In the embodiment of FIG. 7, the housing and magnet means are substantially the same as that of FIG. 6 except that the sensing coil is in the form of a spiral rather than a helix.

The above described method and apparatus provide a means of obtaining a relative indication or value of the concentration of wear debris in a lubricating fluid. It is possible, using the same apparatus, to obtain relatively accurate estimates of both mean particle size and absolute wear debris concentration as explained hereinbelow.

If detector response is plotted against trapping magnet current, then extrapolation to zero response gives a positive intercept on the current axis. The zero response intercept can be regarded as representing the situation in which the attractive force exerted on a stationary ferromagnetic particle by the magnetic field is just balanced by the viscous drag force exerted on the particle by the oil flowing past it. Since large particles are more readily trapped than small ones, it is possible to estimate particle size by determining the zero response intercept. This would constitute useful confirmatory evidence of increased rate of wear since the latter is always accompanied by a shift to larger means particle size. Once the effective particle size has been determined, corresponding calibration data will enable wear debris concentrations to be expressed, quantitatively, in mg.kg.$^{-1}$ (ppm).

In practive, then, this method involves the steps of (a) passing a sample of the fluid through a fluid conduit having an electromagnet associated therewith for trapping within the conduit ferromagnetic wear debris in the fluid and a detector for producing an output signal proportional to the concentration of ferromagnetic wear debris in the lubricating fluid at the trapping site, (b) determining the value of the current passing through the electromagnet at which the output of the detector is zero and (c) converting the value of the current to a mean particle size value. Step (b) is effected by adjusting the magnitude of the electrical current applied to the electromagnet until the output of the detector is zero while step (c) is effected by multiplying the value of the current by a predetermined proportionality constant to produce the mean particle size value. It will be understood that steps (b) and (c) may be conducted manually be manual adjustment of the magnet current or automatically by having a microprocessor, or other electrical circuitry, monitor detector output and magnet current, determine the zero intercept and determine the effective mean particle size and estimate of absolute wear debris concentration.

It will be understood that various other modifications and alterations may be made to the present invention without departing from the spirit of the appended claims.

The embodiment of the invention in which an exclusive property or privilege is claimed are defined as follows:

1. A device for producing an electrical signal which is proportional to the concentration of ferromagnetic particulate material in a fluid stream, said device comprising, in combination:
   a sensing coil arranged to form the inductance coil of and connected to a radio frequency oscillator arranged to produce an electrical signal at a base frequency;
   magnetic trap means for producing a magnetic field; and
   support means for supporting said sensing coil and said magnetic trap measn in juxtaposition to one another such that, when said coil is disposed within or proximate said fluid stream and electrically connected to radio frequency oscillator, energization of said magnetic trap means causes ferromagnetic particulate material proximate said coil to be attracted toward said coil resulting in a deviation of the frequency of said signal from said base frequency proportional to the concentration of ferromagnetic particulate material in said fluid stream.

2. A device as defined in claim 1, wherein the base frequency of said oscillator is about 34 MHz.

3. A device as defined in claim 1, wherein said trap is an electromagnet coaxially disposed about said coil.

4. A device as defined in claim 1, wherein said trap is an electromagnet coaxially disposed within said coil.

5. A device as defined in claim 1, wherein said support means includes non-magnetic, electrical insulating means connecting said coil and said magnetic trap means.

6. A device as defined in claim 5, wherein said insulating means is an epoxy matrix.

7. A device as defined in claim 1, wherein said trap means is adapted to be selectively energized and de-energized.

8. A device for producing an electrical signal which is proportional to the concentration of ferromagnetic particulate material in a fluid, said device comprising, in combination:
   a housing having a fluid passage extending therethrough;
   a radio frequency oscillator for producing an electrical signal at a predetermined base frequency, said oscillator having an inductance coil disposed in said housing in coaxial relation with respect to said passage;
   magnetic trap means disposed in said housing in electrically insulated relation with respect to said inductance coil, said magnetic trap means being arranged to produce a magnetic field about said inductance coil such that energization of said magnetic trap means causes ferromagnetic particulate material in said passage and proximate said coil to be attracted toward said coil and results in a deviation of the frequency of said signal from said base frequency proportional to the concentration of ferromagnetic particulate material in said fluid stream.

9. A device as defined in claim 8, said inductance coil forming in part a surface of said passage whereby trapped ferromagnetic particulate material is magnetically urged aganist said surface.

10. A device as defined in claim 8, further including means for selectively energized and de-energizing said magnetic trap means.

11. A device as defined in claim 8, said magnetic trap means being electromagnet disposed in said housing concentrially about inductance coil.

12. A device as defined in claim 8, further including means for determining the magnitude of said deviation and a quantity linearly related to the concentration of ferromagnetic particulate material in fluid passing through said passage.

13. A device as defined in calim 12, said quantity being the ratio of the magnitude of said deviation to the duration of said deviation.

14. A device as defined in claim 12, said means including a microprocessor.

15. A device as defined in claim 8, wherein the base frequency of said oscillator is about 34 MHz.

16. An apparatus for monitoring to rate if wear of a machine emeploying a lubricating fluid for lubricating ferromagnetic components which produce ferromagnetic particulate wear debris during operation, said apparatus comprising, in combination:
   a detector for producing an electrical signal proportional to the concentration of ferromagnetic particulate material in said fluid, said detector including a housing a fluid passage extending therethrough a radio frequency oscillator for producing an electrical signal at a predetermined base frequency, said oscillator having an inductance coil disposed in said housing in coaxial relation with respect to said passage, magnetic trap means disposed in said housing in electrically insulates relation with respect to said inductance coil, said magnetic trap means being arranged to produce a magnetic field about said inductance coil such that energization of said magnetic trap means causes ferromagnetic particualte material in said passage and proximate said coil to be attracted toward said coil and results in a deviation of the frequency of said signal from said base frequency proportional to the concentration of ferromagnetic particulate material in said fluid stream;

control means for energizing and de-energizing said magnetic trap means at predetermined timed intervals;

means for determining, at the end of each said predetermined timed interval, a quantity linearly related to the concentration of ferromagnetic partoculate material in fluid passed through said detector, determining the rate of change of said quantities and activating an alarm means when the rate of change of said quantity exceeds a predetermined threshold value.

17. A device as defined in claim 16, further including timing means for determining a time interval within which said magnetic trapping means is energized.

18. A device as defined in claim 17, further including counter means for counting the number of cycles of said output signal during said time interval and means responsive to a predetermined count for de-activating said timing means and thereafter de-energizing said magnetic trap means.

19. A device as defined in claim 18, further including means for activating said timing means at a predetermined time interval after energizing said magnetic trap means.

20. A device as defined in claim 16, said responsive means including timing means, counter means and microprocessor means, said microprocessor means being adapted to signal said control means whereby to energize said magnetic trap means at equal predetermined timed intervals, activate said timing means and said counter means at a predetermined time interval after energizing said trap means, deactivate said timing means and counter means when the count of said counter means attains a predetermined value, and thereafter de-activate said trap means, and determine a quantity related to the concentration of the ferromagnetic particulate material in said lubrication fluid.

21. A method of determining a quantity related to the concentratoin of ferromagnetic material in a fluid, comprising the steps of:
    (a) passing a sample of said fluid through a fluid conduit;
    (b) electromagnetically trapping ferromagnetic particulate material at a predetermined site in said fluid conduit at which an inductance coil of a radio frequency oscillator is coaxially disposed;
    (c) determining the deviation, during said electromagnetically trapping step, of the frequency of the output signal of said oscillator from a reference signal; and
    (d) determining the ratio of said deviation to the duration of said deviation, said ratio being linearly proportional to the concentration of said ferromagnetic particulate material in said fluid.

22. A method as defined in claim 21, wherein said step of determining said deviation including determining the change in frequency of said signal during said electromagnetically trapping step for a predetermined, fixed trapping interval.

23. A method as defined in claim 21, wherein said step of determining said deviation including determining the trapping interval within which the frequency of said signals attains a predetermined value.

24. A method as defined in claim 21, wherein said step of determining said deviation including determining the number of cycles of the frequency of said signal which occur within a fixed, predetermined trapping interval.

25. A method as defined in claim 21, wherein said step of determining said deviation including determining the trapping interval within which the number of cycles of the frequency of said signal reaches a predetermined value.

26. A method of determining the degree of wear of a machine having ferromagnetic components subjected to wear during operation resulting in the production of frerromagnetic particulate material, said machine having a lubrication system utilizing a lubrication fluid, in which said ferromagnetic particulate material becomes entrained, for lubricating said components, said method comprising the steps of:
    (a) determining, at predetermined intervals of time, a quantity related to the concentration of ferromagnetic particulate material in said fluid in accordance with the method of claim 22;
    (b) determining the rate of change of said quantity, a substantially constant rate of change of concentration being indicative of nornal wear and a non-linear, increasing rate of change of concentration being indicative of excessive wear of said machine.

27. A method of determining the degree of wear of a machine having ferromagnetic components subjected to wear during operation resulting in the production of feromagnetic particulate material, said machine having a lubrication system utilizing a lubrication fluid, in which said ferromagnetic particulate material becomes entrained, for lubricating said components, said method comprising the steps of:
    (a) determining, at pedetermined intervals of time, a quantity related to the concentration of ferromagnetic particulate material in said fluid in accordance with the method of claim 22;
    (b) determining the rate of change of said quantity, a substantially constant rate of change of concentration being indicative of normal wear and a non-linear, increasing rate of change of concentration being indicative of excessive wear of said machine.

28. A method of determining the degree of wear of a machine having ferromagnetic components subjected to wear during operation resulting in the production of ferromagnetic particulate material, said machine having a lubrication system utilizing a lubrication fluid, in which said ferromagnetic particulate material becomes entrained, for lubricating said components, said method comprising the steps of:
    (a) passing a sample of said fluid through a fluid conduit having (i) an electromagnet concentrically disposed thereabout at a predetermined site thereof and (ii) an inductance coil of an oscillator circuit coaxially disposed with respect to said conduit at said site;
    (b) energizing said electromagnet to trap ferromagnetic particulate material at said site;
    (c) activating a timing means to determine a trapping interval;
    (d) counting the number of cycles of the signal of said oscillator circuit which occur within said trapping interval;
    (e) deactivating said timing means when said count reaches a predetermined value;
    (f) de-energizing said electromagnet;

(g) determining the ratio of said count to said trapping interval;

(h) repeating steps (a) to (e) at fixed predetermined time intervals; and (i) determining the rate of change of said ratio and activating an alarm means if said rate of change exceeds a predetermined threshold level.

29. A method of determining the effective means particle size of ferromagnetic wear debris in a lubricating fluid, comprising the steps of:

(a) passing a sample of said fluid through a fluid conduit having an electromagnet associated therewith for trapping within said conduit ferromagnetic wear debris in said fluid and a detector for producing an output signal proportional to the concentration of ferromagnetic wear debris in said lubricating fluid at said trapping site;

(b) determining the value of the current passing through said electromagnet at which the output of said detector is zero;

(c) converting said value of said current to a number indicative of the mean particle size of said ferromagnetic wear debris.

30. A method as defined in claim 29, wherein step (b) includes the step of adjusting the magnitude of the electrical current applied to said electromagnet until the output of said detector is zero.

31. A method as defined in claim 29, wherein step (c) incudes the step of multiplying said value of said current by a predetermined proportionality constant to produce said number.

32. A method as defined in claim 29, wherein step (b) includes the step of adjusting the magnitude of the electrical current applied to said electromagnet until the output of set detector is zero; and wherein step (c) includes the step of multiplying said value of said current by a predetermined proportionality constant to produce said number.

* * * * *